United States Patent [19]

Millay et al.

[11] Patent Number: 5,014,714
[45] Date of Patent: May 14, 1991

[54] METHOD AND APPARATUS FOR DISTINGUISHING BETWEEN ACCURATE AND INACCURATE BLOOD PRESSURE MEASUREMENTS IN THE PRESENCE OF ARTIFACT

[75] Inventors: Jack M. Millay; Richard A. Walloch, both of Beaverton, Oreg.

[73] Assignee: SpaceLabs, Inc., Redmond, Wash.

[21] Appl. No.: 383,207

[22] Filed: Jul. 19, 1989

[51] Int. Cl.$^5$ .................................................. A61B 5/02
[52] U.S. Cl. ...................................... 128/672; 128/680; 128/682
[58] Field of Search ............................ 128/672, 677–686

[56] References Cited

U.S. PATENT DOCUMENTS

| | | | |
|---|---|---|---|
| 4,360,029 | 11/1982 | Ramsey, III | 128/681 |
| 4,543,962 | 10/1985 | Medero et al. | 128/682 |
| 4,638,810 | 1/1987 | Ramsey, III et al. | 128/682 X |
| 4,754,761 | 7/1988 | Ramsey, III et al. | 128/683 |

Primary Examiner—Ruth S. Smith
Assistant Examiner—J. P. Lacyk
Attorney, Agent, or Firm—Seed and Berry

[57] ABSTRACT

A system for determining if a blood pressure measurement made by an automatic blood pressure monitor has been adversely affected by artifact. The system first compares the diastolic, mean arterial and systolic pressures to respective average diastolic, mean arterial and systolic pressures. If all three of these pressures are within a predetermined range of their corresponding average pressures and if the relationship between these pressures conforms to a physiologically realistic model, then the diastolic, mean arterial and systolic pressures obtained from a measurement are considered valid. If more than one of these pressures is outside the predetermined range of its corresponding average pressure, then the measurement is considered to be adversely affected by artifact and is rejected. If only one of these pressures is outside the predetermined range of its corresponding average pressure, then a replacement pressure is calculated for that pressure. The replacement pressure is calculated based on the pressures that are within the predetermined range and on an average of pressures from previous measurements.

30 Claims, 7 Drawing Sheets

METHOD AND APPARATUS FOR DISTINGUISHING BETWEEN ACCURATE AND INACCURATE BLOOD PRESSURE MEASUREMENTS IN THE PRESENCE OF ARTIFACT

DESCRIPTION

1. Field of the Invention

This invention relates to the automatic measurement of blood pressure, and more particularly to a method and apparatus for screening out blood pressure measurements that are inaccurate because of artifact while allowing blood pressure measurements to be used if such measurements are accurate despite the presence of artifact.

2. Background Art

Automatic blood pressure monitors are commonly used to periodically measure the blood pressure of a patient. In most automatic blood pressure monitors, a pressure cuff is attached to a patient's arm over the brachial artery. The cuff is first pressurized with an applied pressure that is high enough to substantially occlude the brachial artery. The cuff pressure is then gradually reduced, either continuously or in increments. As the pressure is reduced to systolic pressure, the flow of blood through the brachial artery beneath the cuff increases substantially.

When the blood flows through the brachial artery following each contraction of the heart, it imparts a pulsatile movement to the wall of the artery. This pulsatile movement is coupled to a blood pressure cuff extending over the artery as minute changes in the cuff pressure, which are known as oscillometric pulses. Automatic blood pressure monitors measure and record the amplitude of the oscillometric pulses at a number of cuff pressures. After the blood pressure measurement had been completed, a table contains the oscillometric pulse amplitudes recorded at each cuff pressure.

In theory, the systolic, diastolic, and means arterial blood pressures can then be determined from the values in the table using empirical definitions of these parameters as a function of the amplitudes of these oscillometric pulses. However, blood pressure measurements are often adversely affected by artifact, generally produced by patient movement. Motion-induced artifact can substantially alter the measured amplitude of oscillometric pulses thus introducing inaccuracies in the measurement of the patient's blood pressure.

Techniques have been developed to screen blood pressure measurements for artifacts. Some of these techniques may employ (a) the interval between oscillometric pulses or Korotkoff sounds or (b) the internal consistency of the oscillometric pulses, or (c) the relationship between oscillometric pulses, Korotkoff sounds and/or the QRS-complex of an EKG. Regardless of the method used to screen the blood pressure results, certain blood pressure measurements will fail the screening procedure. Measurements that fail the screening procedure are generally discarded and the doctor/patient is given a message indicating the reason for the failure of the measurement.

All screening procedures suffer from two forms of error. The first type of error results from false positives, i.e., the screening procedure may accept an INACCURATE measurement that should have been rejected. The second type of error results from false negatives, i.e., the screening procedure may reject an accurate measurement that should have been accepted. As the screening procedure is made more stringent to minimize false positives, more false negatives will inherently occur.

DISCLOSURE OF THE INVENTION

The primary object of the invention is to provide a method and apparatus for rejecting blood pressure measurements that are rendered inaccurate by artifact while allowing use of blood pressure measurements made in the presence of artifact as long as the artifact has not adversely affected the accuracy of such measurements.

It is another object of the invention to provide an improved screening technique that allows acceptance criteria to be sufficiently stringent to avoid false positive errors without inducing false negative errors.

It is still another object of the invention to provide an improved screening technique that can be adapted for use with virtually any commercially available automatic blood pressure monitor.

These and other objects of the invention are provided by the addition of a second screening procedure to screening procedures that are conventionally used in automatic blood pressure monitors. After the first screening procedure indicates that artifacts were present during the blood pressure measurement, the second screening procedure determines whether or not those artifacts adversely affected the accuracy of the measurement. That determination is preferably made by comparing the current results with previously recorded results. The internal consistency of the intervals separating oscillometric pulses at each cuff pressure is preferably used as the first screening procedure to indicate the presence of artifact.

BEST MODE FOR CARRYING OUT THE INVENTION

Figure 1:
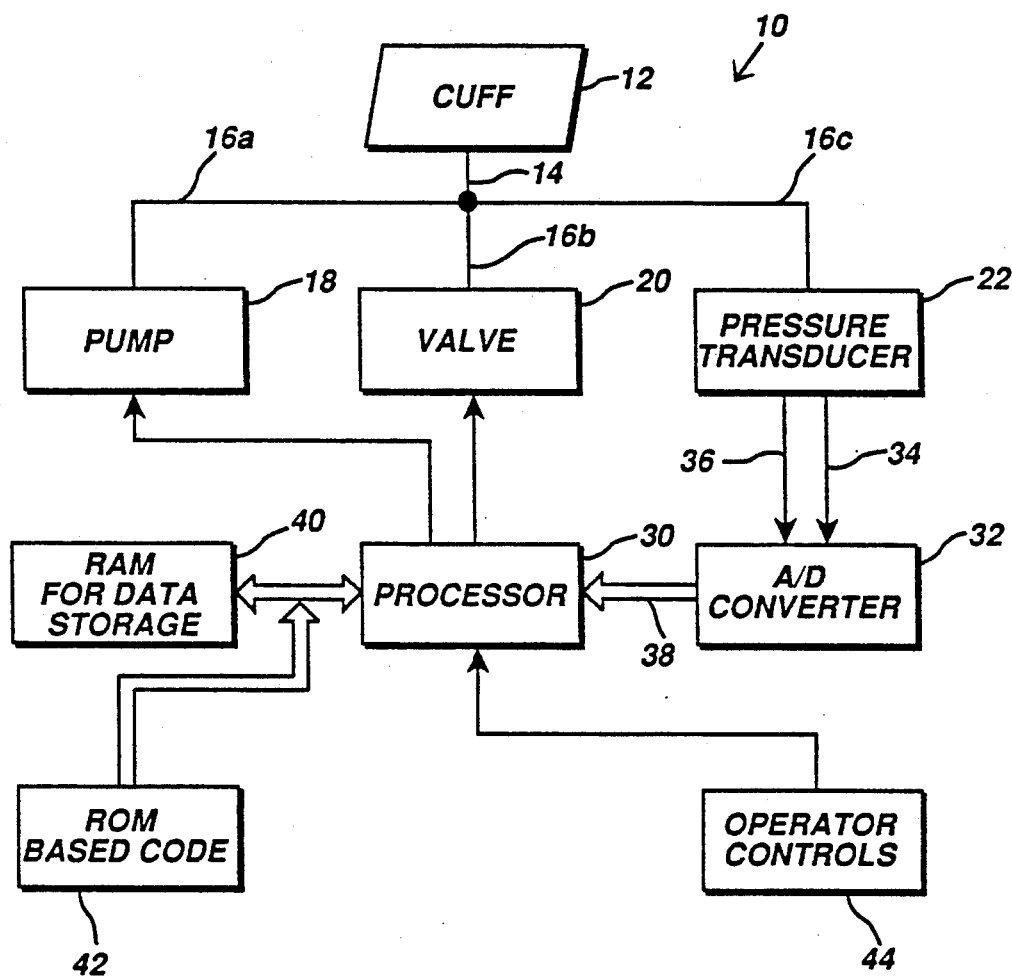
FIG. 1 is a block diagram of an automatic blood pressure monitor using the inventive system for distinguishing between accurate and INACCURATE measurements in the presence of artifact.

One embodiment of a system for screening against the deleterious effects of artifact in an automatic blood pressure measuring system is illustrated in FIG. 1. The system 10 is composed of a number of hardware components, all of which are conventional. The system includes a conventional blood pressure cuff 12 in fluid communication with conduits 14 and 16, a conventional pump 18 a conventional valve 20, and a conventional pressure transducer 22. The pump 18 and valve 20 are operated by a conventional microprocessor 30.

As explained in greater detail below, during the operation of the automatic blood pressure measuring system, the blood pressure cuff 12 is inflated to a pressure that is greater than systole as indicated by the pressure transducer 22. The valve 20 is then opened, usually for a predetermined period, although it may be continuously open to allow a slight leakage of air from the blood pressure cuff 12. However, the valve 20 normally allows air to escape from the cuff 12 fairly rapidly in relatively small increments. As the pressure in the cuff 12 is reduced, either gradually or incrementally, the pressure in the cuff 12 is measured by the pressure transducer 22.

The pressure in the blood pressure cuff 12 consists of two components, namely, a relatively constant, or "DC", component and a relatively variable, or "AC", component. The relatively constant component is a function of the pressure in the blood pressure cuff 12. The relatively variable component is produced by the minute change in the pressure of the cuff 12 following each contraction of the heart. Thus, the relatively constant DC component of the pressure in the cuff can be used as an indication of cuff pressure, while the relatively variable AC component of the pressure in the cuff 12 can be used as an indication of an oscillometric pulse.

Two signals are obtained from the pressure transducer. One set of circuitry 34 supplies a DC component to an analog-to-digital (A/D) converter 32. Another set of circuitry 36 supplies an AC component to the A/D converter 32. The signal supplied through the DC circuitry 34 is thus an indication of the cuff pressure, while the signal supplied through the AC circuitry 36 is an indication of the oscillometric pulse. The A/D converter 32 digitizes the DC and the AC signals and outputs digital bytes indicative of their values through a bus 38 to the microprocessor 30.

As mentioned above, the microprocessor 30 is of conventional variety and, as is typical with such devices, is connected to a random access memory 40 used for the storage of data, and to either random access memory or read-only memory 42 that contains the software for operating the microprocessor 30. Operator controls 44, such as a keyboard or buttons, are also connected to the microprocessor 30.

Although the measuring system 10 illustrated in FIG. 1 utilizes a pressure transducer 22 and separate circuitry for the AC and the DC pressure signals, it will be understood that other implementations are possible. For example, a single circuit providing a signal corresponding to both the steady-state and the variable pressures in the cuff 12 can be supplied to the analog-to-digital converter 32. After the signal is digitized by analog-to-digital converter 32 and applied to the microprocessor 30, algorithms executed by the microprocessor 30 can detect the steady-state component of the cuff pressure and the variable component variations in the cuff pressure.

Figure 2A:
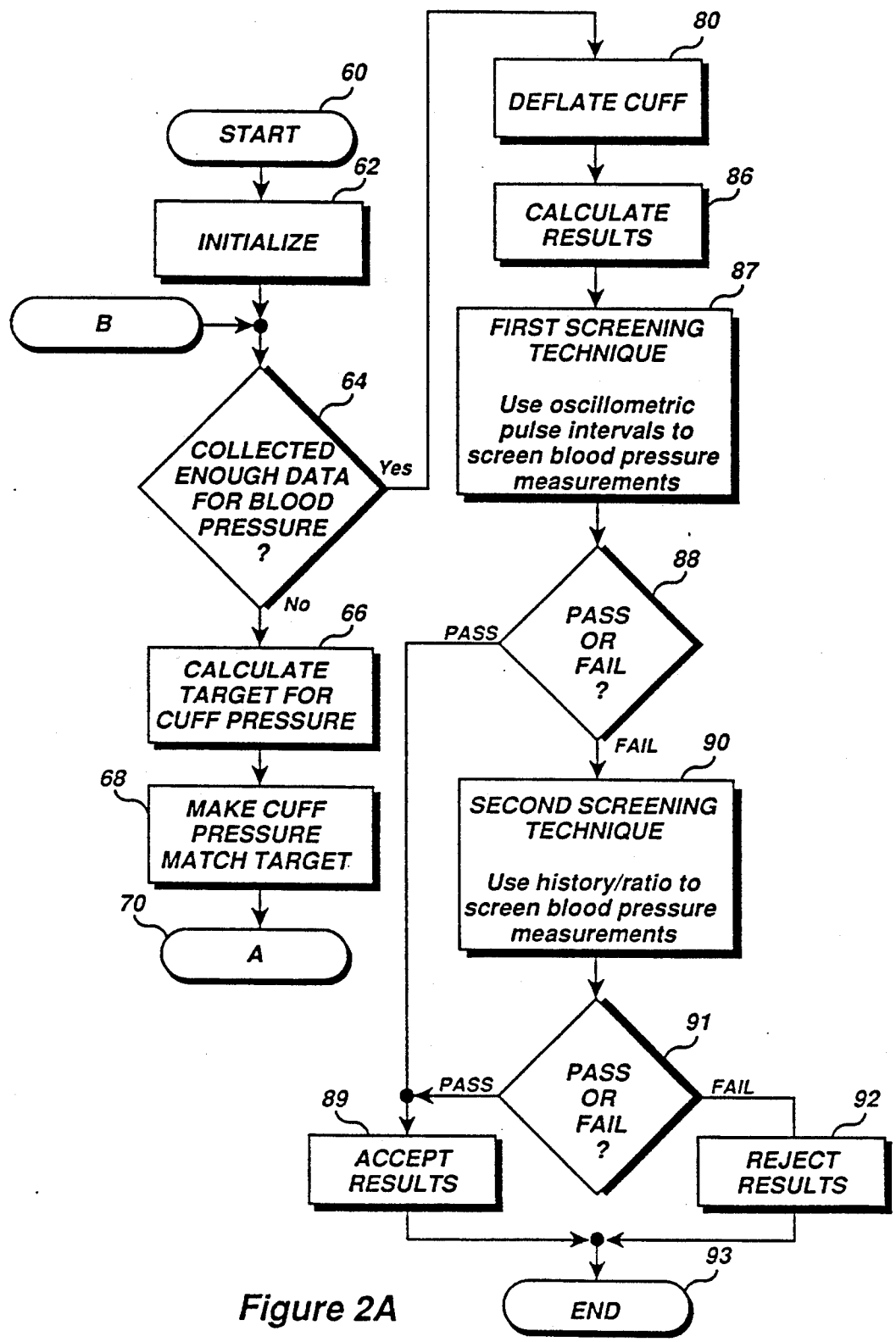
FIGS. 2A and 2B are flow charts of software controlling the operation of a processor used in the system of FIG. 1.
Figure 2B:
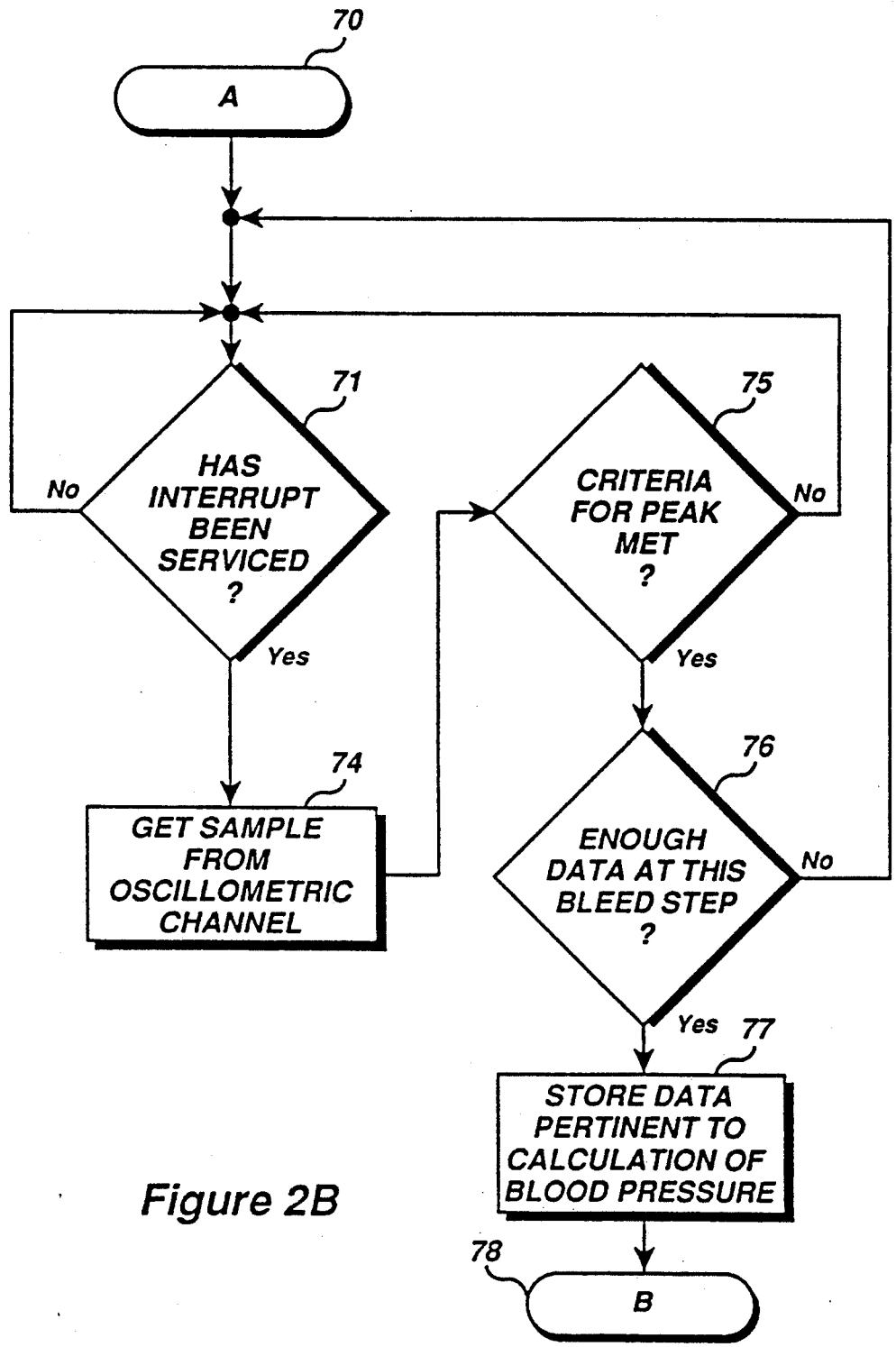

As explained above, the microprocessor 30 is controlled by software that is stored as a series of program instructions in the memory 42. A flow chart from which object code can be easily and quickly written by one skilled in the art is illustrated in FIGS. 2A and 2B. With reference to FIG. 2A, the program starts at 60, either through an operator command, automatically at power-up or when call by another program stored in the memory 42. As is conventional with microprocessor-base systems, the system is initialized at 62 to set up the software for subsequent processing, such as, for example, establishing tables that will subsequently contain data, by setting flags and by setting variables to known values. The program then checks at 64 to determine if enough data has been collected to provide a blood pressure measurement. The decision block 64 is first encountered prior to obtaining any blood pressure data. Thus, when the program initially encounters decision block 64, enough data for a blood pressure determination will not have been collected. As a result, the program will branch to 66 to calculate a target value for the pressure in the blood pressure cuff 12 (FIG. 1). The target pressure for the cuff 12 will, of course, be in excess of the cuff pressure before the measurement is started. The microprocessor 30 then energizes the pump 18 (FIG. 1) at 68 while measuring the DC signal as digitized by the analog-to-digital convertor 32. The microprocessor continues to energize the pump 18 at 68 until the cuff pressure is equal to the target pressure. On subsequent passes through steps 66 and 68, the target pressure calculated at 66 will be lower than the pressure in the cuff 12. The microprocessor 30 will thus energize the valve 20 at 68 to reduce the pressure in the cuff 12 to the target pressure.

The program progresses from 68 in FIG. 2A to 71 in FIG. 2B. The microprocessor 30 is interrupt driven in a conventional manner so that it periodically performs a clock driven interrupt service routine. The program waits at 71 until the interrupt has been serviced. The program then processes the digitized AC signal output at 74 and establishes the proper criteria for a set of samples being considered an oscillometric pulse. The program then checks at 75 to see if the criteria established at 74 have been met. The criteria for determining if a set of samples is characteristic of an oscillometric pulse are conventional and are thus not explained herein. If the samples are not characteristic of an oscillometric pulse, the program returns to 71 to await another interrupt. If the samples do have the characteristics of an oscillometric pulse, the program branches to 76 to see if enough data had been collected at the current cuff pressure i.e. does the oscillometric peak meet amplitude and timing constraints of the algorithm? If enough data have not been collected, the program returns to 71 to await another interrupt, and then processes another sample at 74 and 75 as explained above, before once again checking for sufficient data at 76. If the program determines at 76 that all of the pertinent data needed at a given cuff pressure had been collected, the program stores the data at 77 in appropriate tables. The DC component of the cuff pressure is stored along with amplitude and timing data of the AC oscillometric pulses. The program then returns via 78 to 64 to determine whether or not enough oscillometric pulses have been collected to determine the patient's blood pressure. The program will continue to loop through 64–78 until data have been obtained sufficient to allow the calculation of the patient's blood pressure.

The data stored in the table after sufficient data have been obtained may appear for example as:

| CUFF PRESSURE | PULSE AMPLITUDE |
| --- | --- |
| 150 | 0 |
| 140 | 50 |
| 130 | 92 |
| 120 | 100 |
| 110 | 97 |
| 100 | 75 |
| 90 | 50 |

| -continued | |
|---|---|
| CUFF PRESSURE | PULSE AMPLITUDE |
| 80 | 25 |
| 70 | 10 |

The interval between oscillometric pulses are also stored and these data are used to calculate the heart rate as well as screen for motion artifacts.

Once the program determines at 64 that sufficient data have been collected to determine a blood pressure, the program will then branch from 64 to 80, where the microprocesor 30 will continuously deflate the cuff 12.

The program then calls subroutines to calculate (a) systole, (b) diastole and (c) mean arterial pressure 86. The algorithm to calculate systole and diastole is described in U.S. Pat. No. 4,785,820 entitled Method And Apparatus For Systolic Blood Pressure Measurements which is incorporated herein by reference. The algorithm to calculate mean arterial pressure is described in U.S. patent application Ser. No. 299,776 entitled Method And Apparatus For Determining The Mean Arterial Pressure In Automatic Blood Pressure Measurements which is incorporated herein by reference. Therefore, in the interests of brevity, a complete explanation of these algorithms will not be included herein.

An oscillometric pulse is produced by the flow of blood beneath the blood pressure cuff subsequent to each contraction of the heart. The interval between oscillometric pulses is thus indicative of the heart rate. Data indicative of the interval of time between subsequent oscillometric pulses is stored at 77. The heart rate is determined from this data at 86 along with the calculation of systole, diastole, and mean arterial pressure.

In 87, the intervals between oscillometric pulses collected at each blood pressure are used to screen the measurement using an algorithm described in U.S. Pat. No. 4,777,959 entitled Artifact Detection Based On Heart Rate In A Method And Apparatus For Indirect Blood Pressure Measurement which is incorporated herein by reference. The technique for calculation of the heart rate is also described in that patent application. In the interest of brevity, the algorithms will not be described in detail, although the rationale on which the algorithms are based will be briefly described.

The average interval between oscillometric pulses is calculated for all pertinent data. The single interval which is most deviant from the average is found. If that most deviant interval is within some limit, the calculated average is accepted; it is converted into beats per minute. However, if the most deviant interval is outside the specification, it is discarded; and the average interval is re-calculated without that discarded interval. The process is repeated until the most deviant interval is within specification.

The data collected at cuff pressures where the oscillometric pulse intervals have been discarded are logically suspect. (If the interval is incorrect, what can be said of the amplitude). If enough data are suspect to throw doubt upon systole, diastole or mean arterial pressure then the blood pressure measurement fails the first screening technique 87. The exact algorithm that decides whether or not to accept the blood pressure will not be repeated here.

At 88, a decision of whether or not the blood pressure passed the first screening technique is made. If the measurement passes, the results are accepted, displayed to the user and stored for future recall at 89.

In present blood pressure monitoring systems, a failure at 88 would cause the measurement to be discarded. An event code would be displayed for the user and stored for later recall. The present invention inserts a second screening process after the fail decision had been made at 88. This second screening process is implemented at steps 90 and 91.

The stored data of previous blood pressure measurements are analyzed at 90 according to the second screening process, as described in greater detail below. At 91, a decision is made as to whether or not the blood pressure measurement passed this second screening process. If the measurement passed, the algorithm branches to 89, where the results are accepted, displayed to the user and stored for future recall. If the stored data fails the second screening process, the algorithm branches to 92, where an event code is displayed and stored. In either case, the program ends at 93. At 93, the program may turn the power of the unit off, or return to the program which initially called it.

Figure 3A:
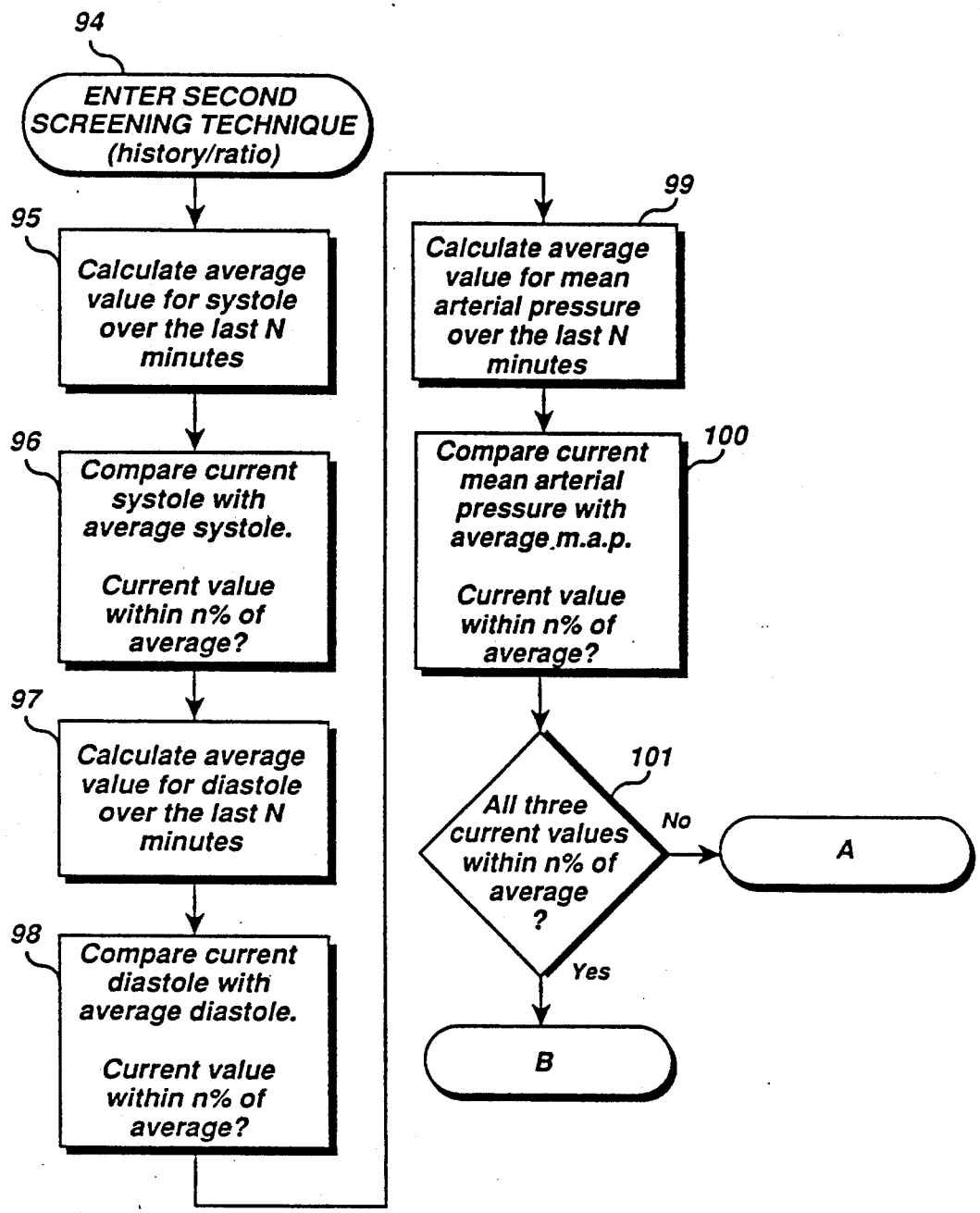
FIGS. 3A, 3B and 3C are flow charts of an algorithm used in the program shown in FIG. 2 to reject blood pressure measurements that have been adversely affected by artifact while accepting blood pressure measurements that have not been adversely affected by artifact.
Figure 3B:
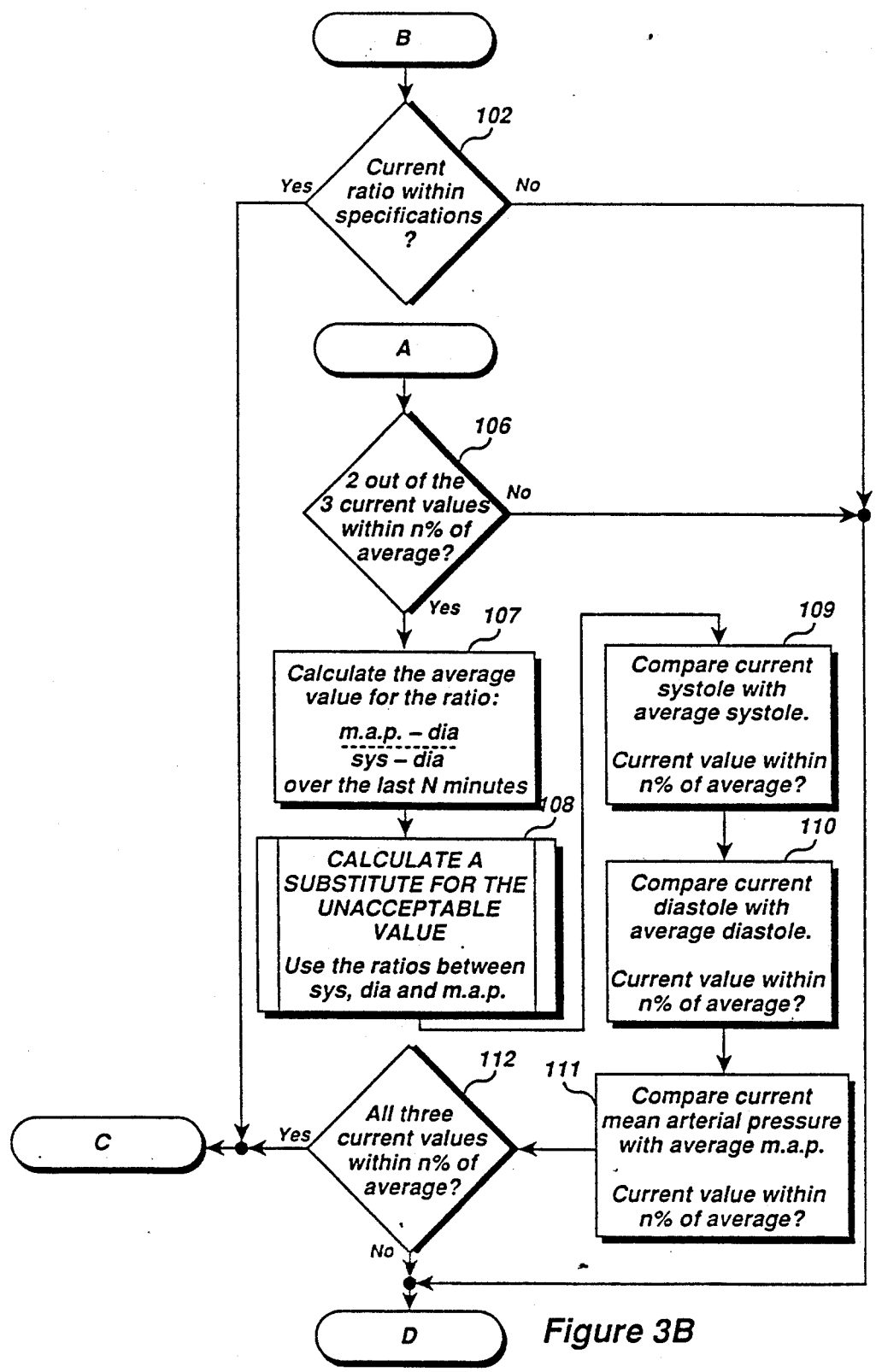
Figure 3C:
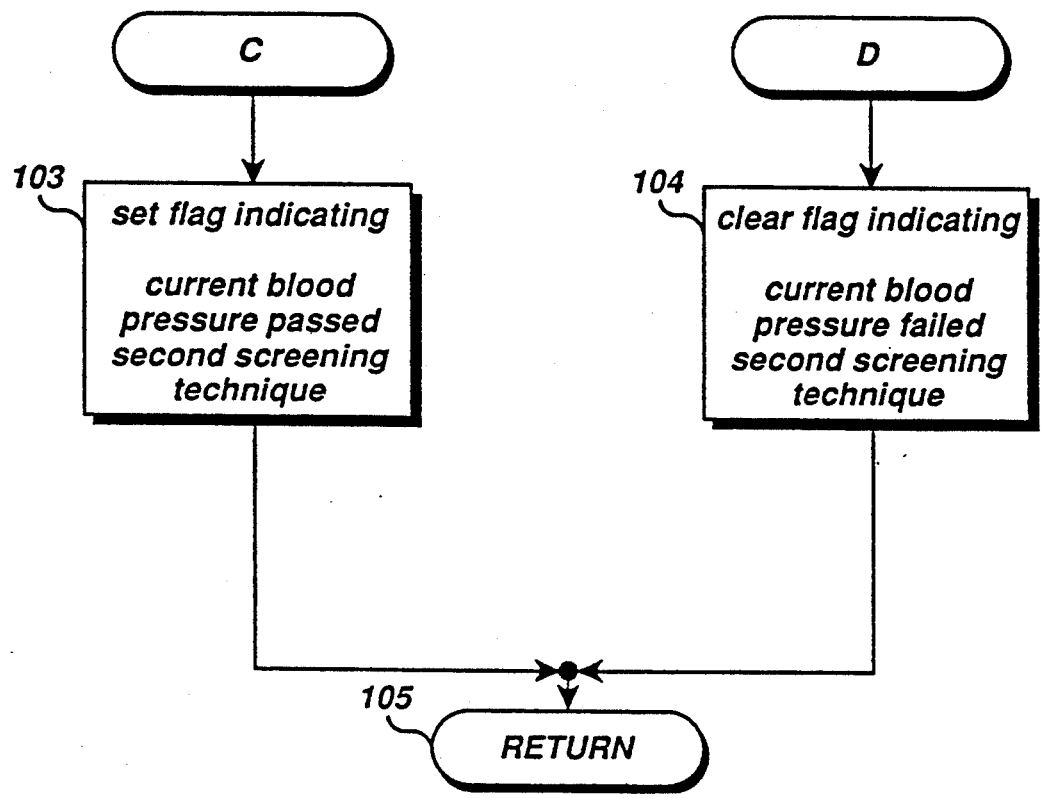

The second screening process, which is shown in FIG. 3, begins at 94. At 95, the average value for systole collected over some time period is calculated. In the current implementation a time period of 140 minutes is used. In this implementation, blood pressures are usually taken every 20 minutes while the patient is awake and once an hour while sleeping. Therefore, there is an opportunity to average 7 readings during waking hours and 2 readings during the sleeping hours.

In the present implementation, only blood pressure measurements that passed the first screening test are included into the averages. If the blood pressure monitor had been turned off and then on, only measurements obtained after the unit was turned on are used in calculating the average.

After the average value of systole is calculated at 95, the current systole is compared to the calculated average at 96. To meet specifications, the current value of systole must be within 12.5% of the calculated average systole. A flag is set at 96 if the current value of systole is within this predetermined ranges and it is cleared in the current value of systole is outside this predetermined range. The algorithm is repeated for diastole at 97 and 98 and for mean arterial pressure at 99 and 100.

The status of each of the flags set or cleared at 96, 98, 100 is examined at 101 to determine whether or not they are all set, i.e., all three parameters (systole, diastole, and mean arterial pressure) are within 12.5% of the calculated averages of these parameters. If they are within this predetermined range, the program branches to 102. Here the parameter RATIO defined as:

$$\text{RATIO} = \frac{\text{MEAN ARTERIAL PRESSURE} - \text{DIASTOLE}}{\text{SYSTOLE} - \text{DIASTOLE}}$$

The RATIO is measure of the location of the mean arterial pressure between the diastolic and systolic pressures. For example, a RATIO of 0.5 means that the mean arterial pressure is midway between the diastolic and systolic pressures. If the RATIO is between 0.15 and 0.45, then the ratio is judged within specification and the program branches to 103. A flag is then set at 103 to indicate that the blood pressure measurement passed the second screening process. If the RATIO is not between 0.15 and 0.45 at 102, the program branches to 104, where the flat is cleared before the subroutine returns 105 to the main program. Thus, even if the measurement failed the first screening process, it will nevertheless be considered accurate if (a) the systolic, diastolic and mean arterial pressures are within a predetermined range of the average of these pressures over an extended period of time and (2) if the relationship between the systolic, diastolic and mean arterial pressures are physiologically realistic, i.e. the mean arterial pressure is larger than the diastolic pressure by 15%–45% of the difference between the systolic and diastolic pressures.

If one or more of the three values (diastolic, systolic and mean arterial pressures) are found to be outside of the predetermined ranges at 101, then the program branches to 106. Here, the status of each of the flags set or cleared at 96, 98, 100 is examined to determine whether or not two out of the three flags are set, i.e., two out of three parameters are within 12.5% of the average calculated for that value.) If two values are outside of that predetermined range, then the program branches to 104 where an event code is displayed to the user and stored for later recall.

If two out of the three values are found to be within the predetermined range at 106, then the program branches to 107. Here an average of the RATIO calculated at 102 over an extended period of time is calculated. However, a RATIO for a measurement is used only if the measurement:
(a) passed the first screening test;
(b) occurred less than 140 minutes ago;
(c) occurred since the power had been turned on; and
(d) yielded a RATIO of between 0.15 and 0.45.

The program then proceeds to 108 were a value is calculated to replace the value (i.e., diastolic, systolic or mean arterial pressure) that was not within a predetermined range of the average of such value. This value is calculated at 108 as a function of the two values that were within the predetermined range using an algorithm described below. This calculated replacement and the values that were within the predetermined range are compared with the average values of previously stored readings for systole at 109, diastole at 110, and mean arterial pressure at 111. These comparisons 109, 110, and 111 verify that the calculated replacement value meets the specifications of the second screening technique.

The flags indicating whether or not the three values are within the predetermined range are checked at 112. If the flag for all three values are found to be set (i.e., the values are within the predetermined range), then the program branches to 103 were a flag is set to indicate that the measurement passed the second screening process. If all three of the flags are not found to be set at 112, the program branches to 104, where the flag is cleared, indicating that the measurement failed the second screening process.

Upon return via 105 to the calling program, the status of the pass or fail flag is checked at 91. Then the program either branches to 89 to accept, display and store the results or it branches to 92 to reject the results and display and store an event code.

As explained above with reference to FIG. 3, a replacement value is calculated at 108 in the event that a measured blood pressure value (i.e., diastolic, systolic or mean arterial pressure) was not within a predetermined range of the average of such value. This value is calculated at 108 as a function of the two values that were within the predetermined range. The algorithm used to perform this calculation is illustrated in FIG. 4.

Figure 4:
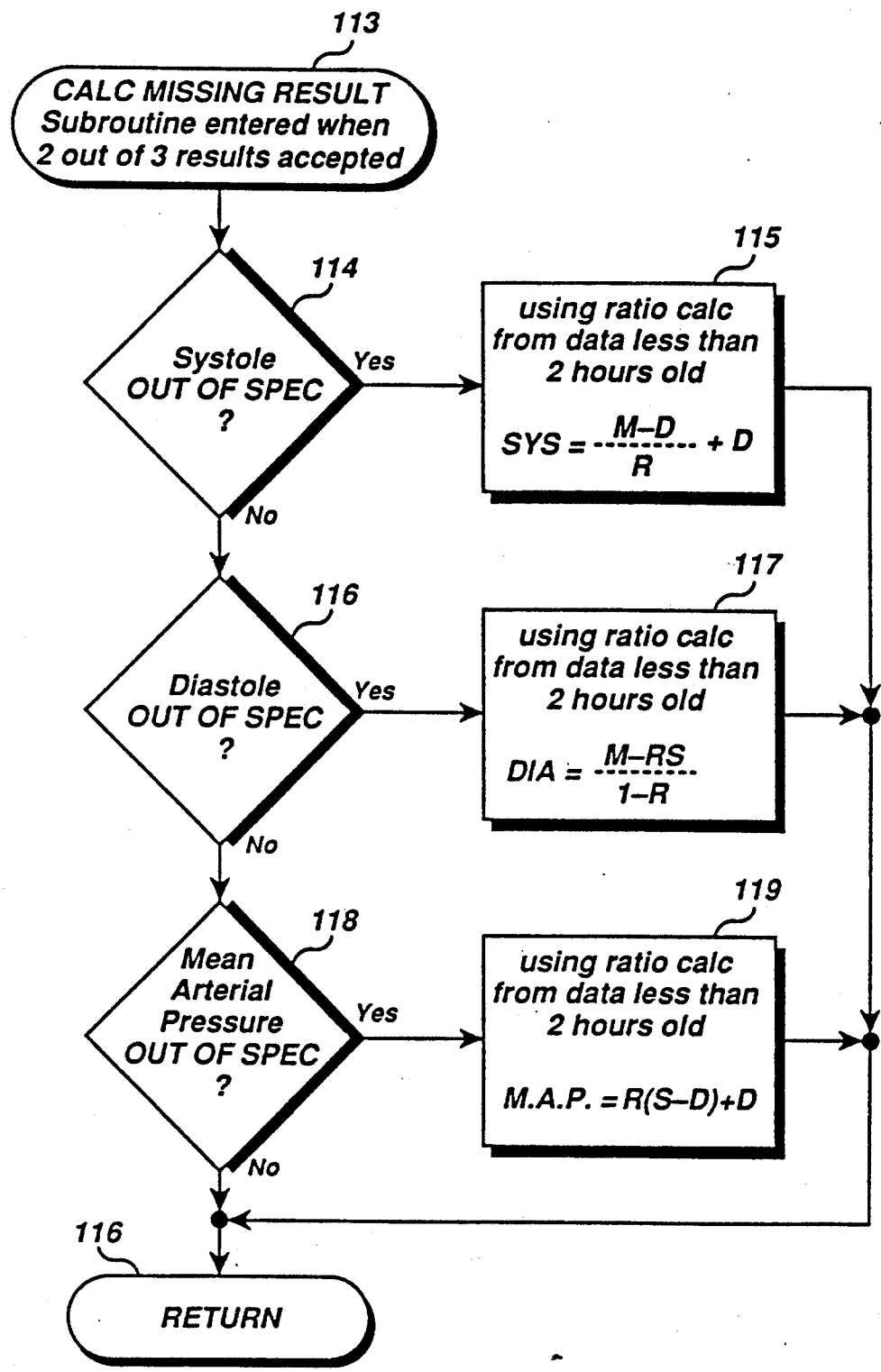
FIG. 4 is a flow chart of an algorithm used in the program shown in FIG. 3 to calculate a value of a blood pressure variable that is used to replace a value that has been adversely affected by artifact.

With reference, now, to FIG. 4, the subroutine is entered at 113, and a decision is made at 114 as to whether a replacement value for systole needs to be calculated. If a systole replacement needs to be calculated, the program branches to 115. The replacement systole value is calculated by the following formula:

$$\text{SYSTOLE} = \frac{\text{MEAN ARTERIAL PRESSURE} - \text{DIASTOLE}}{\text{AVG. RATIO}} + \text{DIASTOLE}$$

In the above formula, Avg. RATIO is the average of ratios calculated as a function of previously stored measurements which were calculated in 107. The replacement systole value is essentially the sum of the current diastole value and the difference between the average systole and diastole values except that the difference between the average systole and diastole values are first multiplied by a correction factor. The correction factor is equal to the ratio of the difference between the current mean arterial and diastole values to the average mean arterial and diastole values. The correction factor is, in effect, a measure of how the current systole value can be expected to deviate from the average systole value based on how the difference between the current mean and diastole values differ from the average mean and diastole values.

If a measurement is to be included in the calculation of Avg. RATIO, the measurement must have:
(a) occurred within the last 140 minutes;
(b) occurred since the power switch had been turned on;
(c) passed the first screening technique 86, 87; and
(d) had a ratio have been between 0.15 and 0.45.

The Avg. RATIO used to calculate a replacement systolic value is given by:

$$\text{AVG. RATIO} = \frac{\text{AVG. MEAN ARTERIAL PRESSURE} - \text{AVG. DIASTOLE}}{\text{AVG. SYSTOLE} - \text{AVG. DIASTOLE}}$$

After systole is calculated at 115, the program returns to the calling program through 116. If a replacement value of systole is calculated, there is no reason to check diastole and mean arterial since the subroutine illustrated in FIG. 4 is called only if one value is outside the predetermined range.

If the blood pressure value that was outside of the predetermined range was not systole, the program branches to 116 to determine whether the current diastole value was within the predetermined range. If the diastole value was not within range, the program branches to 117 where a replacement diastole value is calculated by the following formula:

$$\text{DIASTOLE} = \frac{\text{MEAN ARTERIAL PRESSURE} - (\text{AVG. RATIO})(\text{SYSTOLE})}{1 - \text{RATIO}}$$

The replacement diastole value is essentially the current systole value less the difference between the average systole and diastole values except that the average systole and diastole values are first multiplied by a correction factor. The correction factor is equal to the ratio of the difference between the current systole and mean arterial values to the difference between the average systole and mean arterial values. The correction factor is, in effect, a measure of how the current diastole value can be expected to deviate from the average diastole value based on how the difference between the current systole and mean arterial values differ from the average systole and mean arterial values.

After diastole has been calculated at 117, the program returns to the calling program through 116. If a replacement value of diastole is calculated, there is no reason to check the mean arterial value since the subroutine illustrated in FIG. 4 is called only if a single value is outside the predetermined range.

If the blood pressure value that was outside of the predetermined range was not either systole or diastole, the program branches to 118 to determine whether the current mean arterial pressure value was within the predetermined range. If the mean arterial value was within range the program returns to the calling program 116 without modifying any of the values since an error in the calling program must exist because the subroutine illustrated in FIG. 4 should not have been entered unless one and only one of the values were outside the predetermined range.

If the mean arterial value is found to not be within the predetermined range at 118, the program branches to 119 where a replacement mean arterial value is calculated by the following formula:

Mean Arterial Pressure = Avg.
Ratio(Systole − Diastole) + Diastole

After the mean arterial pressure had been calculated, the program returns to the calling program through 116.

We claim:

1. A blood pressure monitor, comprising:
a blood pressure cuff;
an air pump pneumatically coupled to said blood pressure cuff;
a valve pneumatically coupled to said blood pressure cuff;
a pressure transducer pneumatically coupled to said blood pressure cuff, said pressure transducer generating a signal indicative of the air pressure in said blood pressure cuff and a signal corresponding to oscillometric pulses in said blood pressure cuff;
processor means connected to said pressure transducer and receiving said signal indicative of the air pressure in said blood pressure cuff and said signal corresponding to oscillometric pulses in said blood pressure cuff, said processor means energizing said air pump to inflate said blood pressure cuff, periodically energizing said valve to incrementally reduce the air pressure in said blood pressure cuff, recording the cuff pressure at which each measurement is made and the amplitude of the oscillometric pulses at such cuff pressure, calculating the diastolic, mean arterial and systolic pressures from said table of cuff pressures and oscillometric pulse amplitudes, calculating the average of the diastolic, mean arterial and systolic pressures recorded in said table for a plurality of measurements, comparing the diastolic, mean arterial and systolic pressures recorded in said table for a current measurement to the average of the diastolic mean, arterial and systolic pressures, respectively, and then determining whether artifact has adversely affected the accuracy of any pressure recorded in said table for a current measurement by determining whether a predetermined number of said pressures recorded in said table for a current measurement deviates from their corresponding average pressures by a predetermined value.

2. The blood pressure monitor of claim 1 wherein said processing means further compares the relationship between the systolic, diastolic and mean arterial pressures to a physiologically realistic model and determines that said current measurement has been adversely affected by artifact if the relationship between the systolic, diastolic or mean arterial pressure varies from said physiologically realistic model by a predetermined value.

3. The blood pressure monitor of claim 2 wherein said processing means compares the relationship between the systolic, diastolic and mean arterial pressures to a physiologically realistic model by calculating the ratio of the difference between said mean arterial pressure and said diastolic pressure to the difference between said systolic pressure and said diastolic pressure.

4. The blood pressure monitor of claim 3 wherein said processing means determines whether the relationship between the systolic, diastolic and mean arterial pressures varies from said physiologically realistic model by a predetermined value by determining if said ratio is within a predetermined range.

5. The blood pressure monitor of claim 4 wherein said predetermined range if between 0.15 and 0.45.

6. The blood pressure monitor of claim 1 wherein said processing means calculates a replacement pressure for each of said current pressures that said processing means determines has deviated from its corresponding average pressure by a predetermined value.

7. The blood pressure monitor of claim 6, wherein said processing means calculates a replacement diastolic pressure according the formula:

$$\text{DIASTOLE} = \frac{\text{MEAN ARTERIAL PRESSURE} - (\text{AVG. RATIO})(\text{SYSTOLE})}{1 - \text{RATIO}}$$

where AVG. RATIO is calculated according to the formula:

$$\text{AVG. RATIO} = \frac{\text{AVG. MEAN ARTERIAL PRESSURE} - \text{AVG. DIASTOLE}}{\text{AVG. SYSTOLE} - \text{AVG. DIASTOLE}}$$

8. The blood pressure monitor of claim 6, wherein said processing means calculate a replacement systolic pressure according the formula:

$$\text{SYSTOLE} = \frac{\text{MEAN ARTERIAL PRESSURE} - \text{DIASTOLE}}{\text{AVG. RATIO}} + \text{DIASTOLE}$$

where AVG. RATIO is calculated according to the formula:

$$\text{AVG. RATIO} = \frac{\text{AVG. MEAN ARTERIAL PRESSURE} - \text{AVG. DIASTOLE}}{\text{AVG. SYSTOLE} - \text{AVG. DIASTOLE}}$$

9. The blood pressure monitor of claim 6, wherein said processing means calculated a replacement mean arterial pressure according the formula:

MEAN ARTERIAL PRESSURE = AVG. RATIO (SYSTOLE − DIASTOLE) + DIASTOLE where AVG. RATIO is calculated according to the formula:

$$\text{AVG. RATIO} = \frac{\text{AVG. MEAN ARTERIAL PRESSURE} - \text{AVG. DIASTOLE}}{\text{AVG. SYSTOLE} - \text{AVG. DIASTOLE}}$$

10. The blood pressure monitor of claim 6 wherein said processing means calculates a replacement pressure as long as two of the pressures recorded in said table for said current measurement have not deviated from their corresponding average pressures by said predetermined value.

11. A blood pressure monitor, comprising:
a blood pressure cuff;
an air pump pneumatically coupled to said blood pressure cuff;
a valve pneumatically coupled to said blood pressure cuff;
a pressure transducer pneumatically coupled to said blood pressure cuff, said pressure transducer generating a signal indicative of the air pressure in said blood pressure cuff and a signal corresponding to oscillometric pulses in said blood pressure cuff;
processor means connected to said pressure transducer and receiving said signal indicative of the air pressure in said blood pressure cuff and said signal corresponding to oscillometric pulses in said blood pressure cuff, said processor means energizing said air pump to inflate said blood pressure cuff, periodically, energizing said valve to incrementally reduce the air pressure in said blood pressure cuff, recording the cuff pressure at which each measurement is made and the amplitude of the oscillometric pulses at such cuff pressure, calculating the diastolic, mean arterial and systolic pressures from said table of cuff pressures and oscillometric pulse amplitudes, comparing the relationship between the systolic, diastolic and mean arterial pressures to a physiologically realistic model and determining that said measurement has been adversely affected by artifact if the relationship between the systolic, diastolic or mean arterial pressure varies from said physiologically realistic model by a predetermined value.

12. The blood pressure monitor of claim 11 wherein said processing means compares the relationship between the systolic, diastolic and mean arterial pressures to a physiologically realistic model by calculating the ratio of the difference between said mean arterial pressure and said diastolic pressure to the difference between said systolic pressure and said diastolic pressure.

13. The blood pressure monitor of claim 12 wherein said processing means determines whether the relationship between the systolic, diastolic and mean arterial pressures varies from said physiologically realistic model by a predetermined value by determining if said ratio is within a predetermined range.

14. The blood pressure monitor of claim 13 wherein said predetermined range is between 0.15 and 0.45.

15. A system for calculating a replacement from a table of data containing the diastolic, systolic and mean arterial pressures obtained from a plurality of blood pressure measurements in the event that the accuracy of one of said pressures is adversely affected by artifact, said system comprising:
means for identifying a pressure in said table that has been adversely affected by artifact; and
means for calculating said replacement pressure based on the pressures in said table that have not been adversely affected by artifact and on pressures in said table from previous blood pressure measurements. said system calculating a replacement diastolic pressure according to the formula:

$$\text{DIASTOLE} = \frac{\text{MEAN ARTERIAL PRESSURE} - (\text{AVG. RATIO})(\text{SYSTOLE})}{1 - \text{RATIO}}$$

where AVG. RATIO is calculated according to the formula:

$$\text{AVG. RATIO} = \frac{\text{AVG. MEAN ARTERIAL PRESSURE} - \text{AVG. DIASTOLE}}{\text{AVG. SYSTOLE} - \text{AVG. DIASTOLE}}$$

16. A system for calculating a replacement from a table of data containing the diastolic, systolic and mean arterial pressures obtained from a plurality of blood pressure measurements in the event that the accuracy of one of said pressures is adversely affected by artifact, said system comprising:
means for identifying a pressure in said table that has been adversely affected by artifact; and
means for calculating said replacement pressure based on the pressures in said table that have not been adversely affected by artifact and on pressures in said table from previous blood pressure measurements. said system calculating a replacement systolic pressure according to the formula:

$$\text{SYSTOLE} = \frac{\text{MEAN ARTERIAL PRESSURE} - \text{DIASTOLE}}{\text{AVG. RATIO}} + \text{DIASTOLE}$$

where AVG. RATIO is calculated according to the formula:

$$\text{AVG. RATIO} = \frac{\text{AVG. MEAN ARTERIAL PRESSURE} - \text{AVG. DIASTOLE}}{\text{AVG. SYSTOLE} - \text{AVG. DIASTOLE}}$$

17. A system for calculating a replacement from a table of data containing the diastolic, systolic and mean arterial pressures obtained from a plurality of blood pressure measurements in the event that the accuracy of one of said pressures is adversely affected by artifact, said system comprising:
means for identifying a pressure in said table that has been adversely affected by artifact; and
means for calculating said replacement pressure based on the pressures in said table that have not been adversely affected by artifact and on pressures in said table from previous blood pressure measurements, said system calculating a replacement mean arterial pressure according to the formula:

$$\text{MEAN ARTERIAL PRESSURE} = \text{AVG. RATIO} \cdot (\text{SYSTOLE} - \text{DIASTOLE}) + \text{DIASTOLE}$$

where AVG. RATIO is calculated according to the formula:

$$\text{AVG. RATIO} = \frac{\text{AVG. MEAN ARTERIAL PRESSURE} - \text{AVG. DIASTOLE}}{\text{AVG. SYSTOLE} - \text{AVG. DIASTOLE}}$$

18. A method of determining whether the diastolic, mean arterial and systolic pressures obtained from a blood pressure measurement have been adversely affected by artifact, said method comprising:
   calculating the average of the diastolic, mean arterial and systolic pressures for a plurality of measurements;
   comparing the diastolic, mean arterial and systolic pressures for said measurement to the average of the diastolic, mean arterial and systolic pressures, respectively; and
   determining whether a predetermined number of said pressures obtained by said measurement deviates from their corresponding average pressures by a predetermined value thereby determining whether artifact has adversely affected the accuracy of any pressure obtained by said measurement.

19. The method of claim 18 further comprising:
   comparing the relationship between the systolic, diastolic and mean arterial pressures to a physiologically realistic model; and
   determining that said measurement has been adversely affected by artifact if the relationship between the systolic, diastolic or mean arterial pressure varies from said physiologically realistic model by a predetermined value.

20. The method of claim 19 wherein the relationship between the systolic, diastolic and mean arterial pressures is compared to a physiologically realistic model by calculating the ratio of the difference between said mean arterial pressure and said diastolic pressure to the difference between said systolic pressure and said diastolic pressure.

21. The method of claim 20 wherein said step of determining whether the relationship between the systolic, diastolic and mean arterial pressures varies from said physiologically realistic model by a predetermined value is accomplished by determining if said ratio is within a predetermined range.

22. The method of claim 21 wherein said predetermined range is between 0.15 and 0.45.

23. The method of claim 18 further comprising:
   determining if any of said pressures has deviated from its corresponding average pressure by a predetermined value; and
   if any of said pressures has deviated from its corresponding average pressure by a predetermined value, calculating a replacement pressure for said pressure.

24. The method of claim 24, wherein said replacement diastolic pressure is calculated according to the formula:

$$\text{DIASTOLE} = \frac{\text{MEAN ARTERIAL PRESSURE} - (\text{AVG. RATIO})(\text{SYSTOLE})}{1 - \text{RATIO}}$$

where AVG. RATIO is calculated according to the formula:

$$\text{AVG. RATIO} = \frac{\text{AVG. MEAN ARTERIAL PRESSURE} - \text{AVG. DIASTOLE}}{\text{AVG. SYSTOLE} - \text{AVG. DIASTOLE}}$$

25. The method of claim 23, wherein a replacement systolic pressure is calculated according the formula:

$$\text{SYSTOLE} = \frac{\text{MEAN ARTERIAL PRESSURE} - \text{DIASTOLE}}{\text{AVG. RATIO}} + \text{DIASTOLE}$$

where AVG. RATIO is calculated according to the formula:

$$\text{AVG. RATIO} = \frac{\text{AVG. MEAN ARTERIAL PRESSURE} - \text{AVG. DIASTOLE}}{\text{AVG. SYSTOLE} - \text{AVG. DIASTOLE}}$$

26. The method of claim 23, wherein a replacement mean arterial pressure is calculated according the formula:

$$\text{MEAN ARTERIAL PRESSURE} = \text{AVG. RATIO} \cdot (\text{SYSTOLE} - \text{DIASTOLE}) + \text{DIASTOLE}$$

where AVG. RATIO is calculated according to the formula:

$$\text{AVG. RATIO} = \frac{\text{AVG. MEAN ARTERIAL PRESSURE} - \text{AVE. DIASTOLE}}{\text{AVG}} \cdot \text{AVG. SYSTOLE} - \text{AV}$$

27. A method of determining whether the diastolic, mean arterial and systolic pressure obtained from a blood pressure measurement have been adversely affected by artifact, said method comprising:
   comparing the relationship between the systolic, diastolic and mean arterial pressures to a physiologically realistic model; and
   determining that said measurement has been adversely affected by artifact if the relationship between the systolic, diastolic or mean arterial pressure varies from said physiologically realistic model by a predetermined value.

28. The method of claim 27 wherein said step of comparing the relationship between the systolic, diastolic and mean arterial pressures to a physiologically realistic model is accomplished by calculating the ratio of the difference between said mean arterial pressure and said diastolic pressure to the difference between said systolic pressure and said diastolic pressure.

29. The method of claim 28 wherein said step of determining whether the relationship between the systolic, diastolic and mean arterial pressures varies from said physiologically realistic model by a predetermined value is accomplished by determining if said ratio is within a predetermined range.

30. The method of claim 29 wherein said predetermined range is between 0.15 and 0.45.

* * * * *

UNITED STATES PATENT AND TRADEMARK OFFICE
CERTIFICATE OF CORRECTION

PATENT NO.   : 5,014,714

DATED        : May 14, 1991

INVENTOR(S)  : Jack M. Millay; Richard A. Walloch

It is certified that error appears in the above-identified patent and that said Letters Patent is hereby corrected as shown below:

In column 9, claim 1, line 65, please delete "diastolic mean," and substitute therefor -- diastolic, mean --.

In column 13, claim 24, line 66, please delete "claim 24" and substitute therefor -- claim 23 --.

In column 14, claim 27, line 44, please delete "pressure" and substitute therefor -- pressures --.

Signed and Sealed this

Twelfth Day of January, 1993

Attest:

DOUGLAS B. COMER

*Attesting Officer*    *Acting Commissioner of Patents and Trademarks*